(12) United States Patent
Kikuchi et al.

(10) Patent No.: US 9,017,737 B2
(45) Date of Patent: Apr. 28, 2015

(54) USE OF CANNABINOIDS IN COMBINATION WITH AN ANTI-PSYCHOTIC MEDICAMENT

(75) Inventors: Tetsuro Kikuchi, Osaka (JP); Kenji Maeda, Osaka (JP); Geoffrey Guy, Glanvilles Wootton (GB); Philip Robson, Wiltshire (GB); Colin Stott, Wiltshire (GB)

(73) Assignees: GW Pharma Limited, Salisbury (GB); Otsuka Pharmaceutical Co., Limited, Tokyo (JP)

( * ) Notice: Subject to any disclaimer, the term of this patent is extended or adjusted under 35 U.S.C. 154(b) by 80 days.

(21) Appl. No.: 12/811,393

(22) PCT Filed: Dec. 17, 2008

(86) PCT No.: PCT/GB2008/004217
§ 371 (c)(1),
(2), (4) Date: Nov. 2, 2010

(87) PCT Pub. No.: WO2009/087351
PCT Pub. Date: Jul. 16, 2009

(65) Prior Publication Data
US 2011/0038958 A1    Feb. 17, 2011

(30) Foreign Application Priority Data

Jan. 4, 2008    (GB) .................................... 0800390.7

(51) Int. Cl.
A61K 36/00    (2006.01)
A61K 45/06    (2006.01)
A61K 31/05    (2006.01)
A61K 31/35    (2006.01)
A61K 31/352    (2006.01)
A61K 36/185    (2006.01)

(52) U.S. Cl.
CPC ................. *A61K 45/06* (2013.01); *A61K 31/05* (2013.01); *A61K 31/35* (2013.01); *A61K 31/352* (2013.01); *A61K 36/185* (2013.01)

(58) Field of Classification Search
None
See application file for complete search history.

(56) References Cited

U.S. PATENT DOCUMENTS

| | | | |
|---|---|---|---|
| 5,006,528 | A | 4/1991 | Oshiro et al. |
| 2002/0173513 | A1 | 11/2002 | Jordan et al. |
| 2005/0266108 | A1 | 12/2005 | Flockhart et al. |
| 2007/0105914 | A1 | 5/2007 | Armstrong et al. |
| 2008/0015186 | A1 | 1/2008 | Arnone et al. |
| 2010/0168448 | A1 | 7/2010 | Flockhart et al. |

FOREIGN PATENT DOCUMENTS

| | | | |
|---|---|---|---|
| EP | 0 367 141 | A2 | 5/1990 |
| EP | 0 367 141 | B1 | 1/1996 |
| GB | 2434097 | A * | 7/2007 |
| GB | 2438682 | A | 12/2007 |
| WO | WO-02/060423 | A2 | 8/2002 |
| WO | WO-03/087037 | A1 | 10/2003 |
| WO | WO-2004/060374 | A1 | 7/2004 |
| WO | WO-2005/000830 | A1 | 1/2005 |
| WO | WO-2005/020992 | A1 | 3/2005 |
| WO | WO-2005/063761 | A1 | 7/2005 |
| WO | WO-2006/017892 | A1 | 2/2006 |
| WO | WO-2006/054057 | A2 | 5/2006 |
| WO | WO-2006/097605 | A1 | 9/2006 |
| WO | WO 2007/067617 | A2 | 6/2007 |
| WO | WO-2007/136571 | A1 | 11/2007 |
| WO | WO 2007/144328 | A1 | 12/2007 |
| WO | WO-2007/144628 | A1 | 12/2007 |
| WO | WO-2008/133884 | A2 | 11/2008 |

OTHER PUBLICATIONS

Zuardi et al, Cannabidiol monotherapy for treatment-resistant Schizophrenia, Journal of psychopharmacology (Oxford, England), (Sep. 2006) vol. 20, No. 5, pp. 683-686.*
Ozdemir, Aripiprazole Otsuka Pharmaceutical Co Ltd, Current Opinion in Central & Peripheral Nervous System Investigational Drugs (2000), 2(1), 105-111.*
Molden et al, Pharmacokinetic variability of aripiprazole and the active metabolite dehydroaripiprazole in psychiatric patients. Therapeutic drug monitoring, (Dec. 2006) vol. 28, No. 6, pp. 744-749.*
Tschoner et al, Metabolic side effects of antipsychotic medication. International Journal of Clinical Practice (2007), 61(8), 1356-1370.*
Third Party Submission for U.S. Appl. No. 12/811,393 mailed Apr. 6, 2011.
Baidyanath, Ayurveda Sarasamgrahah. 2003;446. Hindi.
D'Agostino et al., Therapeutic targets for schizophrenia. Drugs Fut. 2008;33(11):981-89.
Dasa, Brhat Nighantu Ratnakara (Saligramanighantubhusanam. 1997; vol. 4 (Part VII):169. Sanskrit.

(Continued)

*Primary Examiner* — Qiuwen Mi

(74) *Attorney, Agent, or Firm* — Wolf, Greenfield & Sacks, P.C.

(57) ABSTRACT

The present invention relates to the use of one or more cannabinoids in combination with one or more anti-psychotic medicaments for use in the prevention or treatment of psychosis and psychotic disorders. Preferably the one or more cannabinoids are taken from the group: cannabidiol (CBD); cannabidiolic acid (CBDA); tetrahydrocannbidivarin (THCV); tetrahydrocannbidivarinin acid (THCVA); cannabichromene (CBC); cannabichromenic acid (CBCA); cannabigerol (CBG) and cannabigerolic acid (CBGA). Preferably the anti-psychotic medication is an atypical anti-psychotic medication.

21 Claims, 5 Drawing Sheets

(56) References Cited

OTHER PUBLICATIONS

Khan et al., Ikseer Azam, vol. I. Fourth Edition. 1930:206. Persian.
Khan et al., Miftaah-al-Khazaain. 1930:607-08. Urdu.
Moreira et al., Cannabidiol inhibits the hyperlocomotion induced by psychotomimetic drugs in mice. Eur J Pharmacol. Apr. 11, 2005;512(2-3):199-205.
Russo et al., A tale of two cannabinoids: the therapeutic rationale for combining tetrahydrocannabinol and cannabidiol. Med Hypotheses. 2006;66(2):234-46. Epub Oct. 4, 2005.
Sadanandasarma et al., Rasatarangini. 11th ed. 1979:720-23. Sanskrit.
Zuardi et al., Cannabidiol, a *Cannabis sativa* constituent, as an antipsychotic drug. Braz J Med Biol Res. Apr. 2006;39(4):421-9. Epub Apr. 3, 2006.
Cassano et al., Aripiprazole in the treatment of schizophrenia: a consensus report produced by schizophrenia experts in Italy. Clin Drug Investig. 2007;27(1):1-13.
Kharkevich, Pharmacology. $3^{rd}$ ed. Moscow: Publishing Group "GEOTAR", 2006: 66-71.
Travis et al., Aripiprazole in schizophrenia: consensus guidelines. Int J Clin Pract. Apr. 2005;59 (4):485-95.

* cited by examiner

Aripiprazole (PO) + CBD (IP) on CAR

Aripiprazole (PO) + THCV (IP) on CAR

Combination Effect of Aripiprazole and THCV on CAR (1)

Combination Effect of Aripiprazole and THCV on CAR (2)

Aripiprazole (PO) + CBD/THCV (IP) on Catalepsy & Ptosis

Combination Effect of CBD/THCV on Aripiprazole-induced Catalepsy

Aripiprazole 30, 60, 120 mg/kg (PO) + Vehicle 2

Combination Effect of CBD/THCV on Aripiprazole-induced Catalepsy

Aripiprazole 30, 60, 120 mg/kg (PO) + CBD 120 mg/kg (IP)

Combination Effect of CBD/THCV on Aripiprazole-induced Catalepsy

Aripiprazole 30, 60, 120 mg/kg (PO) + THCV 60 mg/kg (IP)

Combination Effect of CBD on Aripiprazole-induced Ptosis

Aripiprazole 30, 60, 120 mg/kg (PO) + CBD 120 mg/kg (IP)

Combination Effect of THCV on Aripiprazole-induced Ptosis

Aripiprazole 30, 60, 120 mg/kg (PO) + THCV 60 mg/kg (IP)

USE OF CANNABINOIDS IN COMBINATION WITH AN ANTI-PSYCHOTIC MEDICAMENT

RELATED APPLICATIONS

This application is a national stage filing under 35 U.S.C. §371 of international application PCT/GB2008/004217, filed Dec. 17, 2008, which was published under PCT Article 21(2) in English.

BACKGROUND TO THE INVENTION

Psychosis and psychotic disorders are used to describe patients for whom there is a loss of contact with reality.

Psychosis and psychotic disorders can result in a number of symptoms including: hallucinations, where the patient senses things that are not there; delusions, where the patient has beliefs that are not based on reality; problems in clear thinking; and not realising that there is anything wrong with them.

The following list illustrates a number of these disease states, many of which are classified in the "Diagnostic and Statistical Manual of Mental Disorders, Fourth Edition, text revision" (DSM-IV-TR) published by the American Psychiatric Association 2000: schizophrenia; schizophreniform disorder (acute schizophrenic episode); schizoaffective disorder; bipolar I disorder (mania, manic disorder, manic-depressive psychosis); bipolar II disorder; major depressive disorder with psychotic feature (psychotic depression); delusional disorders (paranoia); shared psychotic disorder (shared paranoia disorder); brief psychotic disorder (other and unspecified reactive psychosis); psychotic disorder not otherwise specified (unspecified psychosis); paranoid personality disorder; schizoid personality disorder; and schizotypal personality disorder.

Schizophrenia is a complex disease where the sufferer has difficulty in understanding the difference between real and unreal experiences. A patient suffering from schizophrenia also has difficulty in logical thought and responding with normal emotions in social and other situations.

Schizophrenia can take on different types: the catatonic type, where the patient suffers motor disturbances, stupor, negativity, rigidity, agitation, and inability to care for their personal needs and a decreased sensitivity to painful stimuli; the paranoid type, where the patient suffers with delusional thoughts of persecution or of a grandiose nature; anxiety; anger; violence and argumentativeness; and the disorganised type, where the patient is incoherent and displays regressive behaviour, delusions, hallucinations, inappropriate laughter, repetitive mannerisms and social withdrawal.

Patients may also suffer with symptoms of one or more subtype or may have had an abatement of the prominent symptoms but some features such as hallucinations may remain.

Schizophreniform disorder (acute schizophrenic episode) is characterized by the presence of some of the symptoms of schizophrenia including: delusions, hallucinations, disorganised speech, disorganised or catatonic behaviour, and negative symptoms. The disorder—including its prodromal, active, and residual phases—lasts longer than 1 month but less than 6 months.

Schizoaffective disorder symptoms can vary greatly from patient to patient. Many patients suffer with problems with mood, daily function or intrusive thoughts. Other symptoms can include elevated, inflated or depressed mood; irritability and poor temper control; changes in appetite, energy and sleep; hallucinations (particularly auditory hallucinations); delusions of reference; paranoia; deteriorating concern with hygiene and disorganised or illogical speech.

Schizoaffective disorder features cycles of severe symptoms followed by improvement.

Bipolar I disorder (mania, manic disorder, manic-depressive psychosis) is characterised by mood swings that range from low (feelings of intense depression and despair) to high (feelings of elation, referred to as "mania") and can be mixed, for example a depressed mood may be combined with restlessness and overactivity. Often both depressive and manic episodes are experienced.

Bipolar II disorder is characterised by hypomanic episodes as well as at least one major depressive episode. Hypomanic episodes do not go to the extremes of mania (i.e. do not cause social or occupational impairment, and are without psychotic features). Bipolar II is much more difficult to diagnose, since the hypomanic episodes may simply appear as a period of successful high productivity and is reported less frequently than a distressing depression. Psychosis can occur in manic and major depressive episodes, but not in hypomania. For both disorders, there are a number of specifiers that indicate the presentation and course of the disorder, including "chronic", "rapid cycling", "catatonic" and "melancholic".

Major depressive disorder with psychotic feature (psychotic depression) is characterised in that a patient in addition to suffering from depressive symptoms also suffers from hallucinations or delusions. These patients often become paranoid and may believe that their thoughts are not their own or that others can 'hear' their thoughts.

Delusional disorders (paranoia) are a form of psychosis where the patient has long-lasting paranoid delusions which have no other physical or medical cause. These delusions may also be accompanied by auditory hallucinations.

Shared psychotic disorder (shared paranoia disorder) is a very rare condition in which people close to a mentally ill person share his or her false beliefs (delusions). As an example, a man with schizophrenia may falsely believe that his children are trying to murder him. His wife develops shared psychotic disorder and comes to believe it as well. This disorder usually occurs in long-term relationships and involves two people. However, it can also develop among members of a group, such as within families. It affects women more often than men.

Brief psychotic disorder (other and unspecified reactive psychosis) is characterised by patients who experience an acute psychotic episode lasting longer than one day but less than one month and that may or may not immediately follow an important life stress or a pregnancy (with postpartum onset). This illness usually comes as a surprise as there is no forewarning that the person is likely to break down, although this disorder is more common in people with a pre-existing personality disorder.

Paranoid personality disorder is characterised by an exaggeration of the cognitive modules for sensitivity to rejection, resentfulness, distrust, as well as the inclination to distort experienced events. Neutral and friendly actions of others are often misinterpreted as being hostile or contemptuous. Unfounded suspicions regarding the sexual loyalty of partners and loyalty in general as well as the belief that one's rights are not being recognized is stubbornly and argumentatively insisted upon. Such individuals can possess an excessive self-assurance and a tendency toward an exaggerated self-reference. Pathological jealousy, instinctive aggressive counter-attack, the need to control others, and the gathering of trivial or circumstantial "evidence" to support their jealous beliefs also features.

Schizoid personality disorder (SPD) is characterised by a lack of interest in social relationships, a tendency towards a solitary lifestyle, secretiveness, and emotional coldness. SPD is reasonably rare compared with other personality disorders, its prevalence is estimated at less than 1% of the general population.

Schizotypal personality disorder, is characterized by a need for social isolation, odd behaviour and thinking, and often unconventional beliefs such as being convinced of having extra-sensory abilities.

Psychosis and psychotic disorders are commonly treated with a class of medication known as atypical anti-psychotics.

Atypical anti-psychotics are also known as second or third generation anti-psychotics of which some are approved by the FDA for use in the treatment of psychotic disorders including: schizophrenia; bipolar disorder; mania and other indications.

Atypical anti-psychotics are a heterogeneous group of otherwise unrelated drugs which are grouped as such due to the fact that they work in a different manner to other typical anti-psychotics. Many, but not all atypical anti-psychotics work by acting upon the serotonin and dopamine receptor systems in the brain.

Examples of atypical anti-psychotic medicaments include but are not limited to: aripiprazole; risperidone; paliperidone; ziprasidone; olanzapine; quetiapine; clozapine; sulpiride; amisulpride; iloperidone; cariprazine; asenapine.

Aripiprazole is a third generation antipsychotic. Aripiprazole has activity as an agonist at the serotonin receptors and dopamine receptors, and acts as an agonist or partial agonist at the serotonin 5-HT1A receptor and as an agonist or partial agonist at the dopamine D.sub.2 receptor. Aripiprazole is a dopamine-serotonin system stabilizer.

Anti-psychotic medication is rarely used in children, although recently both risperidone and aripiprazole have received FDA approval for their use in the treatment of schizophrenia and mania or mixed episodes of bipolar disorder in children and adolescents.

The atypical anti-psychotics class of medicaments are most often favoured by physicians in the treatment of psychotic disorders such as schizophrenia, and their use is slowly replacing the use of typical anti-psychotics such as fluphenazine, haloperidol and chlorpromazine.

One characteristic of atypical anti-psychotics is the decreased propensity of these medicaments to cause extrapyramidal side effects in the absence of prolactin elevation.

The side-effects that have been reported for the class of medicaments known as atypical anti-psychotics vary from drug to drug.

The medicaments olanzapine and risperidone have been contra-indicated in elderly patients with dementia due to an increased risk of stroke.

It is also known that atypical anti-psychotics can cause abnormal shifts in sleep patterns and as such result in extreme tiredness and weakness.

Other side effects include tardive dyskinsia (involuntary jerking and facial grimacing), and dystonia (involuntary muscle contractions). In addition some atypical anti-psychotics may cause serious metabolic disorders, similar to those caused by the typical anti-psychotics.

Such metabolic disorders include hyperglycemia and diabetes.

There are also many reports that anti-psychotic drugs lead to a host of side-effects related to the metabolism.

For example, weight gain, insulin resistance, type 1 and 2 diabetes, hyperlipidemia, hyperprolactinemia, and cardiovascular disease are amongst the metabolically related side-effects that patients taking anti-psychotic medication report.

Clearly there is a significant requirement for an efficacious treatment that is able to prevent or treat psychosis or psychotic disorders without resulting in side-effects. In particular the reduction in the incidence of metabolically related side-effects is of great importance as these diseases and conditions can be so disabling that the patient may stop taking their medication in order to alleviate the side-effects.

There are a number of documents which focus on the use of CB1 antagonists in combination with antipsychotics for this purpose.

WO2006/097605 and US 2008/0015186 describe the use of a pyrazole-based cannabinoid receptor (CB1) antagonist, specifically rimonabant, with antipsychotics such as, risperidone, to counter the weight problems, obesity and metabolic disorders associated with the use of such antipsychotics. In other words both drugs independently perform their natural function.

WO2007/136571 relates to the use of CB1 antagonists and inverse agonists in combination with antipsychotic agents.

WO 03/087037 discloses a treatment for mania comprising using a CB1 receptor modulator in combination with an antipsychotic agent.

US2007/0105914 teaches using CB1 receptor modulators in combination with conventional antipsychotic drugs.

WO2005/063761 describes Azabicyclic heterocycles as cannabinoid receptor modulators and suggests these compounds may be used in combination with antipsychotic agents.

WO2005/020992 suggests countering the problem of weight gain associated with many atypical antipsychotics by co-administering a CB1 antagonist.

By and large these documents are speculative in nature suggesting combinations of many different synthetic compounds with little or no support. No one has however specifically investigated using phyto-cannabinoids in combination with antipsychotics.

WO 2006/054057 discloses using the phyto-cannabinoid THCV in the treatment of disease indications associated with the CB1 cannabinoid receptor based on the surprising discovery it is a neutral CB1 antagonist (in contrast to THC which although structurally similar is a CB1 agonist). It suggests using it for the treatment of e.g. obesity and schizophrenia but makes no suggestion of using it in combination with other drugs.

Cannabinoids are a group of chemicals known to activate cannabinoid receptors in cells. These chemicals, which are found in *cannabis* plants, are also produced endogenously in humans and other animals. These are termed endocannabinoids. Synthetic cannabinoids are chemicals with similar structures to plant cannabinoids or endocannabinoids and it is, of course, possible to also make synthetic versions of these plant cannabinoids or endocannabinoids.

Cannabinoids possess the characteristics of being cyclic molecules exhibiting particular properties such as the ability to easily cross the blood-brain barrier, weak toxicity and few side effects.

Plant cannabinoids or phyto-cannabinoids can also be isolated such that they are "essentially pure" compounds. These isolated cannabinoids are essentially free of the other naturally occurring compounds, such as, other minor cannabinoids and molecules such as terpenes.

Essentially pure compounds have a degree of purity up to at least 95% by total weight. Some essentially pure cannabinoids (whether synthetic or isolated) have been suggested to be neuroprotective agents, either by direct antagonism of the NMDA receptor or by reducing the influx of calcium ions into the cell by another means such as binding with cannabinoid receptors.

However, current thinking is such that it is generally believed that *cannabis*, and by implication the phyto-cannabinoids, may be responsible for users (particularly juveniles) developing psychological illnesses. This is mainly due to the condition known as *cannabis* psychosis. *Cannabis* use has been linked to psychosis by several peer-reviewed studies. A 1987 Swedish study claimed a link between *cannabis* use and schizophrenia. More recently, the Dunedin Multidisciplinary Health and Development Study published research showing an increased risk of psychosis for *cannabis* users with a certain genetic predisposition, held by 25% of the population. In 2007, a study published in *The Lancet* and a poll of mental health experts showed that a growing number of medical health practitioners are convinced that *cannabis* use increases susceptibility to mental illness, accounting for 14% of the United Kingdom's psychosis cases.

It is likely that the link between *cannabis* use and psychosis is as a consequence of the high concentration of the psychoactive cannabinoid tetrahydrocannabinol (THC) that is found in most recreational *cannabis*.

Despite the strong prejudice against *cannabis*, the applicant believes there is significant credible evidence supporting the use of certain phyto cannabinoid based medicines in combination with atypical anti-psychotic drugs. The rationale for this is outlined below.

Some plant cannabinoids have been found to be effective agents in the treatment of psychosis or psychotic disorders. For example, the applicant has demonstrated in their co-pending patent application WO 2005/000830 the use of cannabichromene (CBC) type compounds and derivatives in the treatment of mood disorders. The mood disorders to be treated are taken from the group: morbid or clinical depression; unipolar mood disorder; bipolar mood disorder; syndromal depression; panic disorder and anxiety.

Additionally the applicant has also described in their co-pending application PCT/GB2007/0020216 the use of cannabigerol (CBG) type compounds (including cannabigerol propyl analogue (CBGV)) and their derivatives in the treatment of mood disorders. Similarly the mood disorders to be treated are taken from the group: morbid or clinical depression; unipolar mood disorder; bipolar mood disorder; syndromal depression; panic disorder and anxiety.

In addition to the evidence supporting the use of specific cannabinoids in the treatment of psychotic disorders, there is also credible evidence supporting the use of specific cannabinoids to treat a number of diseases or conditions such as for example stroke, diabetes and other metabolic disorders, where use of the atypical anti-psychotic medicaments are contra-indicated.

Thus whilst single cannabinoids might be used in combination with atypical anti-psychotics a preferred approach may be to use combinations of cannabinoids which may or may not be present as a *cannabis* plant extract. Depending on the extract selected it may desirable to selectively remove all or a proportion of THC or THCA from the extract.

SUMMARY OF INVENTION

According to the first aspect of the present invention there is provided the use of one or more phyto-cannabinoids with one or more anti-psychotic medicaments in the manufacture of a pharmaceutical formulation for use in the prevention or treatment of psychosis or a psychotic disorder, wherein the one or more phyto-cannabinoids are administered separately, sequentially or simultaneously to the one or more anti-psychotic medicaments.

Preferably the one or more phyto-cannabinoids are taken from the group: cannabidiol (CBD); cannabidiolic acid (CBDA); tetrahydrocannbidivarin (THCV); tetrahydrocannbidivarinin acid (THCVA); cannabichromene (CBC); cannabichromenic acid (CBCA); cannabigerol (CBG) and cannabigerolic acid (CBGA).

Preferably the plurality of phyto-cannabinoids are present in the form of a *cannabis* plant extract, which depending on the composition of the extract, may have all or a proportion of THC or THCA selectively removed.

More preferably the cannabinoid extract from at least one *cannabis* plant is a botanical drug substance.

Preferably the cannabinoid extract from at least one *cannabis* plant is produced by extraction with supercritical or subcritical $CO_2$.

Alternatively the cannabinoid extract from at least one *cannabis* plant is produced by contacting plant material with a heated gas at a temperature which is greater than 100° C., sufficient to volatilise one or more of the cannabinoids in the plant material to form a vapour, and condensing the vapour to form an extract.

Alternatively the one or more cannabinoids, including phyto-cannabinoids, may be present in a substantially pure or isolated form.

A "substantially pure" preparation of cannabinoid is defined as a preparation having a chromatographic purity (of the desired cannabinoid) of greater than 90%, more preferably greater than 95%, more preferably greater than 96%, more preferably greater than 97%, more preferably greater than 98%, more preferably greater than 99% and most preferably greater than 99.5%, as determined by area normalisation of an HPLC profile.

Preferably the substantially pure cannabinoid used in the invention is substantially free of any other naturally occurring or synthetic cannabinoids, including cannabinoids that occur naturally in *cannabis* plants. In this context "substantially free" can be taken to mean that no cannabinoids other than the target cannabinoid are detectable by HPLC.

Substantially pure cannabinoids can be prepared from a botanical drug substance. A technique has been established by the applicant and is described in their granted United Kingdom patent, GB2393721.

In another aspect of the present invention the cannabinoid is in a synthetic form.

References to cannabinoids, particularly with regard to therapeutic use, will be understood to also encompass pharmaceutically acceptable salts of the cannabinoid. The term "pharmaceutically acceptable salts" refers to salts or esters prepared from pharmaceutically acceptable non-toxic bases or acids, including inorganic bases or acids and organic bases or acids, as would be well known to persons skilled in the art. Many suitable inorganic and organic bases are known in the art.

The scope of the invention also extends to derivatives of cannabinoids that retain the desired activity. Derivatives that retain substantially the same activity as the starting material, or more preferably exhibit improved activity, may be produced according to standard principles of medicinal chemistry, which are well known in the art. Such derivatives may exhibit a lesser degree of activity than the starting material, so long as they retain sufficient activity to be therapeutically effective. Derivatives may exhibit improvements in other properties that are desirable in pharmaceutically active agents such as, for example, improved solubility, reduced toxicity, enhanced uptake, etc.

Preferably, the cannabinoid combined with the anti-psychotic medicament is formulated as a pharmaceutical composition further comprising one or more pharmaceutically acceptable carriers, excipients or diluents.

The invention also encompasses pharmaceutical compositions comprising cannabinoids, or pharmaceutically acceptable salts or derivatives thereof in combination with anti-psychotic medicaments, formulated into pharmaceutical dosage forms, together with suitable pharmaceutically acceptable carriers, such as diluents, fillers, salts, buffers, stabilizers, solubilizers, etc. The dosage form may contain other pharmaceutically acceptable excipients for modifying conditions such as pH, osmolarity, taste, viscosity, sterility, lipophilicity, solubility etc. The choice of diluents, carriers or excipients will depend on the desired dosage form, which may in turn be dependent on the intended route of administration to a patient.

Suitable dosage forms include, but are not limited to, solid dosage forms, for example tablets, capsules, powders, dispersible granules, cachets and suppositories, including sustained release and delayed release formulations. Powders and tablets will generally comprise from about 5% to about 70% active ingredient. Suitable solid carriers and excipients are generally known in the art and include, e.g. magnesium carbonate, magnesium stearate, talc, sugar, lactose, etc. Tablets, powders, cachets and capsules are all suitable dosage forms for oral administration.

Liquid dosage forms include solutions, suspensions and emulsions. Liquid form preparations may be administered by intravenous, intracerebral, intraperitoneal, parenteral or intramuscular injection or infusion. Sterile injectable formulations may comprise a sterile solution or suspension of the active agent in a non-toxic, pharmaceutically acceptable diluent or solvent. Liquid dosage forms also include solutions or sprays for intranasal, buccal or sublingual administration. Aerosol preparations suitable for inhalation may include solutions and solids in powder form, which may be combined with a pharmaceutically acceptable carrier, such as an inert compressed gas.

Also encompassed are dosage forms for transdermal administration, including creams, lotions, aerosols and/or emulsions. These dosage forms may be included in transdermal patches of the matrix or reservoir type, which are generally known in the art.

Pharmaceutical preparations may be conveniently prepared in unit dosage form, according to standard procedures of pharmaceutical formulation. The quantity of active compound per unit dose may be varied according to the nature of the active compound and the intended dosage regime. Generally this will be within the range of from 0.1 mg to 5000 mg per unit dose.

Preferably the one or more anti-psychotic medicaments are atypical anti-psychotic medicaments.

More preferably the atypical anti-psychotic medicament is taken from the group: aripiprazole; risperidone; paliperidone; ziprasidone; olanzapine; quetiapine; clozapine; sulpiride; amisulpride; iloperidone; cariprazine; asenapine.

More preferably the atypical anti-psychotic medicament is aripiprazole, which may be in a form of its pharmaceutically acceptable salt, suitable solvates (hydrate, ethanolate, etc), metabolites, anhydrous crystals, etc, shown in WO2004/060374.

Aripiprazole, also called 7-{4-[4-(2,3-dichlorophenyl)-1-piperazinyl]butoxy}-3,4-dihydro-2(1H)-quin-olinone, is a carbostyril compound and is useful for treating schizophrenia (EP 0 367 141, U.S. Pat. No. 5,006,528). Aripiprazole is also known as 7-{4-[4-(2,3-dichlorophenyl)-1-piperazinyl]bu-toxy}-3,4-dihydrocarbostyril-, Abilify, OPC-14597, OPC-31 and BMS-337039. Aripiprazole possesses 5-HT1A receptor agonist activity, and is known as useful compound for treating types of depression and refractory depressions, such as endogeneous depression, major depression, melancholia and the like (WO 02/060423, U.S. Patent Application 2002/0173513A1). Aripiprazole has activity as an agonist at the serotonin receptors and dopamine receptors, and acts as an agonist or partial agonist at the serotonin 5-HT1A receptor and as an agonist or partial agonist at the dopamine D.sub.2 receptor. Aripiprazole is a dopamine-serotonin system stabilizer. Metabolites of aripiprazole are included within the scope of the present invention. One such metabolite of aripiprazole is called dehydroaripiprazole. Preferred metabolites of aripiprazole included within the present invention are indicated by the following designations: OPC-14857, DM-1458, DM-1451, DM-1452, DM-1454 and DCPP. Aripiprazole and aripiprazole metabolites to be used in the present invention may be any of form, for example, free bases, polymorphisms of every type of crystal, hydrate, salts (acid addition salts, etc.) and the like. Among of these forms, anhydrous aripiprazole crystals B is a preferred form. As to method for preparing the anhydrous aripiprazole crystals B, for example it is prepared by heating aripiprazole hydrate A, the details of which are shown in WO2004/060374.

Dosage of the drug used in the present invention is decided by considering the properties of each constituent drug to be combined, the properties of the drug combination and the symptoms of the patient.

Aripiprazole or a metabolite, such as dehydroaripiprazole, DM-1458, DM-1451, DM-1452, DM-1454 or DCPP will generally be used in an amount of about 0.1 to 100 mg/once a day (or about 0.05 to about 50 mg/twice a day), and more preferably in an amount of about 1 to 30 mg/once a day (or about 0.5 to about 15 mg/twice a day).

Generally, the weight ratio of the cannabinoids to the anti-psychotic medicament is decided by considering the properties of each constitute drug to be combined, the properties of drug combination and the symptoms of the patient. Preferably the weight ratio is in the range of about 1 part by weight of the cannabinoid to about 0.01 to about 500 parts by weight of the anti-psychotic, more preferably 1 part by weight of the cannabinoid to about 0.1 to about 100 parts by weight of the anti-psychotic.

More preferably the cannabinoid is a phyto-cannabinoid which may be present as a synthesised compound, an isolated compound or as an extract containing one or more other phyto-cannabinoids and other plant constituents in varying amounts. The extract may have had individual cannabinoids, such as THC, selectively removed in whole or part.

Examples of suitable phyto-cannabinoid extracts are illustrated in Table 1 below:

The components of the THCV and CBD plant extracts used in the following examples are described in Table 1 below.

TABLE 1 components of exemplary THCV and CBD plant extracts

| | THCV-rich extract (% w/w of extract) | CBD-rich extract (% w/w of extract) |
|---|---|---|
| Primary/Secondary Cannabinoid: | | |
| THC Content | NMT 20% | 2.0-6.5 |
| CBD Content | | 57.0-72.0 |
| THCV Content | NLT 50% | — |

TABLE 1-continued components of exemplary THCV and CBD plant extracts

|  | THCV-rich extract (% w/w of extract) | CBD-rich extract (% w/w of extract) |
|---|---|---|
| Other Cannabinoids: | | |
| Cannabigerol | | 0.8-6.5 |
| Cannabichromene | | 3.0-6.5 |
| Tetrahydrocannabinolic acid | | — |
| Cannabidivarin | | 1.0-2.0 |
| Cannabidiolic acid | | <2.0 |
| Terpenes: | | |
| Monoterpenes | | 0.4 |
| Di/tri-terpenes | | 0.4 |
| Sesquiterpenes | | 2.0 |

Preferably the psychosis or psychotic disorder to be treated is taken from the group: schizophrenia; schizophreniform disorder (acute schizophrenic episode); schizoaffective disorder; bipolar I disorder (mania, manic disorder, manic-depressive psychosis); bipolar II disorder; major depressive disorder with psychotic feature (psychotic depression); delusional disorders (paranoia); shared psychotic disorder (shared paranoia disorder); brief psychotic disorder (other and unspecified reactive psychosis); psychotic disorder not otherwise specified (unspecified psychosis); paranoid personality disorder; schizoid personality disorder; and schizotypal personality disorder.

According to a second aspect of the present invention there is provided the use of one or more phyto-cannabinoids with one or more anti-psychotic medicaments in the manufacture of a pharmaceutical formulation for use in the prevention or treatment of psychosis or a psychotic disorder in children and juveniles, wherein the one or more phyto-cannabinoids are administered separately, sequentially or simultaneously to the one or more anti-psychotic medicaments.

According to a third aspect of the present invention there is provided a method for the treatment or prevention of psychosis or a psychotic disorder, which comprises administering to a subject in need thereof a therapeutically effective amount of one or more phyto-cannabinoids in combination with one or more anti-psychotic medicaments.

The subject may be an adult, child or juvenile.

According to a forth aspect of the present invention there is provided a pharmaceutical formulation for use in the prevention or treatment of psychosis or a psychotic disorder, which comprises one or more phyto-cannabinoids and one or more anti-psychotic medicaments, for administration separately, sequentially or simultaneously.

Certain aspects of this invention are further described, with reference to the following examples and data in which.

SPECIFIC DESCRIPTION

Figure 1:
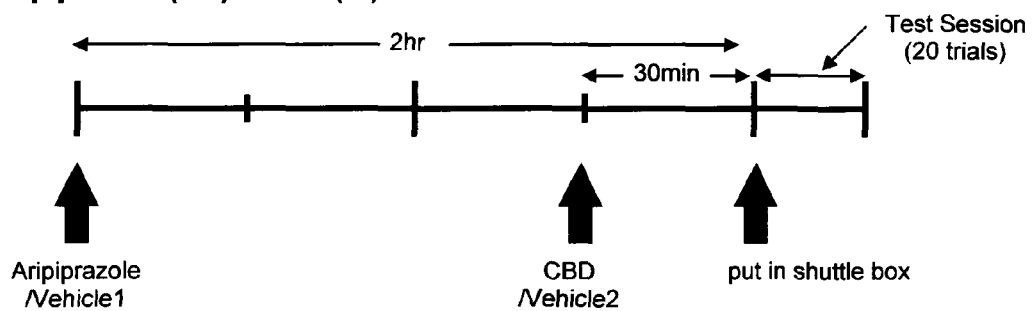
FIG. 1 illustrates the dosing regime in a conditioned avoidance experiment using the cannabinoid CBD with the atypical antipsychotic Aripiprazole APZ.

In addition to the data presented in WO 2005/000830 and PCT/GB2007/0020216, which data indicates that certain cannabinoids act as anti-psychotics per se, there is presented herein further evidence supporting why the use of one or more cannabinoids in combination with an atypical anti-psychotic medicament is likely to be more beneficial than the atypical anti-psychotic alone.

Examples 1 and 2, describe the use of a combination of the cannabinoids tetrahydrocannabivarin (THCV) and cannabidiol (CBD) to in a dietary induced obese mouse model to demonstrate the metabolic effects of the cannabinoids and by implication the potential benefits in counteracting some common side effects resulting from use of atypical anti-psychotics.

Example 3 describes how the cannabinoid CBD is a PPARγ agonist, and provides further evidence of the potential benefits in counteracting some common side effects resulting from use of atypical anti-psychotics by demonstrating that PPARγ ligands have beneficial effects in type 2 diabetes and the cardiovascular system.

Examples 4 to 5 are results obtained from in vivo pharmacological studies:

Example 4 is a conditioned avoidance response study which is an animal model for efficacy and looked at combinations of Aripiprazole with THCV;

Example 5 is a cataleptogenicity study which is an animal model for extrapyramidal side effects and looked at combinations of Aripiprazole with CBD (5a) and THCV (5b).

Example 1

An acute single dose study was undertaken where dietary-induced obese mice were dosed with either:

Pure THCV (0.3 mg/kg)+CBD BDS (CBD at 0.3 mg/kg); or

Pure THCV (3.0 mg/kg)+CBD BDS (CBD at 3.0 mg/kg).

Dietary-induced obese mice are a standard model used to evaluate agents likely to affect metabolic symptoms including obesity, type 1 or 2 diabetes and dyslipidemia. $CB_1$ antagonists are being examined as potential anti-obesity agents and rimonabant has been licensed. Rimonabant shows anti-obesity effects in man and rodent models. Although in rodent models it reduces food intake over the first few days, the long term anti-obesity effect seems to be more related to energy expenditure increases, possibly mediated via increased release of adiponectin from adipose tissue.

THCV and CBD are natural products with significant activity at the $CB_1$ receptor. The example described here was designed to explore anti-obesity and the consequential metabolic effects by measurement of food intake and body weight change after the single dose of the combination of cannabinoids.

Animals were dosed just before lights out and food intake was measured at 2 h, 4 h and 24 h.

Results:

There was no difference in effect after a single dose on the body weight of the study animals dosed with the combination of THCV and CBD in comparison to the control animals after the single dose (data not shown).

However, there was a decrease in the amount of food consumed over 24 hours in the animals treated with the combination of THCV and CBD as shown in Table 2 below.

TABLE 2

Food consumption

|  | Food consumption (g/animal) | | |
| --- | --- | --- | --- |
|  | 2 hours | 4 hours | 24 hours |
| Control | 0.5 | 1.0 | 4.3 |
| THCV + CBD (both 0.3 mg/kg) | 0.5 | 0.8 | 3.8 |
| THCV + CBD (both 3.0 mg/kg) | 0.25 | 0.7 | 3.3 |

As can be seen from the results above the single dose of the combined THCV and CBD resulted in a reduction of food intake within 4 hours of administration. This reduction was still observed at 24 hrs post dose. The reduction in food intake was more marked in the higher dose group.

Example 2

A chronic dosing, 28-day study was undertaken where dietary-induced obese mice were dosed daily at 09:00 by oral gavage with either:
  Pure THCV (0.3 mg/kg)+CBD BDS (CBD at 0.3 mg/kg); or
  Pure THCV (3.0 mg/kg)+CBD BDS (CBD at 3.0 mg/kg).
Animals were acclimatised during Days 1-2 of the study and dosing was started on Day 3.
Measurements were taken to provide data for the following:
  Food and water intake (daily);
  Body weight (twice weekly);
  24 h energy expenditure (Days 3 and 10);
  Oral Glucose Tolerance Test (OGTT, glucose load 3 g/kg) in 5 h-fasted mice (Days 7 and 21);
  Thermic response to a mixed meal (Day 17)
  Body composition (% body fat) by Dexascan in anaesthetised mice (Day 28)
  Nose-anus length measurement (Day 28)
  Blood sample from fed mice for measurement of glucose, lactate, insulin, triglycerides, cholesterol, HDL-cholesterol (Day 28);
  Blood sample from fasted mice for measurement of glucose, free fatty acids, insulin and adiponectin (Day 30); and
  2-3 h post-dosing drug levels & endocannabinoid level (Day 30).

It is advantageous to know whether any anti-obesity effects are a loss of fat mass (desirable) or a proportionate loss of fat and lean tissue (undesirable). These data were achieved via a Dexascan measurement and measurement of the plasma leptin concentration which is known to correlate with adipose tissue mass.

Energy expenditure was measured by indirect calorimetry on two occasions in order to see if there is either tolerance or an induction process. In addition to the 24 h metabolic rate, the thermic response to a mixed meal was determined. Studies on rimonabant have shown an up-regulation of adiponectin mRNA in adipose tissue. This cytokine is now viewed as an important component of the energy balance control system. In addition adiponectin knock-out mice are obese and insulin resistant and administration of recombinant adiponectin to genetic and dietary-induced obese mice reduces fat mass and improves insulin action. Thus, adiponectin might be a mediator of the energy wasting processes.

Loss of body fat and increase in energy expenditure both improve insulin sensitivity. This was determined from glucose and insulin concentrations in 5 h-fasted mice and through measurement of glucose tolerance.

Potential effects on plasma lipids were also determined.

Results:

TABLE 3

Energy expenditure over 24 hours

|  | Energy expenditure (kJ/h/animal) AUC |
| --- | --- |
| Control | 210 |
| THCV + CBD (both 0.3 mg/kg) | 290 |
| THCV + CBD (both 3.0 mg/kg) | 310 |

TABLE 4

Energy expenditure per Kg over 24 hours

|  | Energy expenditure (kJ/h/Kg) AUC |
| --- | --- |
| Control | 4250 |
| THCV + CBD (both 0.3 mg/kg) | 5750 |
| THCV + CBD (both 3.0 mg/kg) | 6500 |

Both the low and the high dose combination of THCV+CBD increased the energy expenditure of the animals 24 hours post dosing.

TABLE 5

Energy expenditure over 3 hours

|  | Energy expenditure (kJ/h/animal) AUC |
| --- | --- |
| Control | 14.0 |
| THCV + CBD (both 0.3 mg/kg) | 21.5 |
| THCV + CBD (both 3.0 mg/kg) | 25.0 |

TABLE 6

Energy expenditure per Kg over 3 hours

|  | Energy expenditure (kJ/h/Kg) AUC |
| --- | --- |
| Control | 400 |
| THCV + CBD (both 0.3 mg/kg) | 510 |
| THCV + CBD (both 3.0 mg/kg) | 500 |

Both the low and the high dose combination of THCV+CBD significantly increased the energy expenditure 3 hours post dosing.

TABLE 7

Bodyweight gain

| | Body weight gain (g) |
|---|---|
| Control | 8.5 |
| THCV + CBD (both 0.3 mg/kg) | 9.5 |
| THCV + CBD (both 3.0 mg/kg) | 9.0 |

Neither the low or high dose of the combination of THCV+CBD reduced the amount of body weight gain in comparison to the control group.

TABLE 8

Food intake per animal

| | Food intake (g/animal) |
|---|---|
| Control | 3.9 |
| THCV + CBD (both 0.3 mg/kg) | 3.5 |
| THCV + CBD (both 3.0 mg/kg) | 3.6 |

Cumulative food intake generally increased over the 28-day dosing period in all groups. The lower dose combination of THCV+CBD produced the smallest intake.

TABLE 9

Glucose tolerance test

| | Glucose tolerance ([Blood Glucose]/animal) | |
|---|---|---|
| | Day 7 | Day 23 |
| Control | 12 | 8 |
| THCV + CBD (both 0.3 mg/kg) | 13 | 11 |
| THCV + CBD (both 3.0 mg/kg) | 18 | 16 |

TABLE 10

Glucose tolerance test (AUC)

| | Glucose tolerance (OGTT AUC 0-120) | |
|---|---|---|
| | Day 7 | Day 23 |
| Control | 2250 | 1950 |
| THCV + CBD (both 0.3 mg/kg) | 2400 | 2200 |
| THCV + CBD (both 3.0 mg/kg) | 2600 | 2500 |

Neither combination of THCV+CBD improved the glucose tolerance of the animals studied.

TABLE 11

Plasma insulin 30 min pre-dose

| | Plasma insulin ([Blood Insulin] pmol/L) | |
|---|---|---|
| | Day 7 | Day 23 |
| Control | 9000 | 13000 |
| THCV + CBD (both 0.3 mg/kg) | 7500 | 11000 |
| THCV + CBD (both 3.0 mg/kg) | 12500 | 8500 |

Plasma insulin levels were improved by the higher dose combination of THCV+CBD.

TABLE 12

Fed glucose levels

| | Glucose levels ([Blood Glucose] mmol/L) |
|---|---|
| Control | 6.0 |
| THCV + CBD (both 0.3 mg/kg) | 10.0 |
| THCV + CBD (both 3.0 mg/kg) | 9.5 |

TABLE 13

Fasted glucose levels

| | Glucose levels ([Blood Glucose] mmol/L) |
|---|---|
| Control | 6.0 |
| THCV + CBD (both 0.3 mg/kg) | 6.8 |
| THCV + CBD (both 3.0 mg/kg) | 7.0 |

The fed and fasted blood glucose concentrations were increased in both study groups in comparison to the control.

TABLE 14

Total body fat

| | Body fat | |
|---|---|---|
| | (g) | (%) |
| Control | 33 | 62.0 |
| THCV + CBD (both 0.3 mg/kg) | 33 | 61.5 |
| THCV + CBD (both 3.0 mg/kg) | 31 | 60.0 |

The amount of body fat in the animals treated with the combination of THCV+CBD had a tendency for reduction particularly at the higher dose. It should be noted that any effect may have been masked by an increased food intake.

TABLE 15

Anus-nose length

| | Lenth (mm) |
|---|---|
| Control | 92.3 |
| THCV + CBD (both 0.3 mg/kg) | 92.5 |
| THCV + CBD (both 3.0 mg/kg) | 91.7 |

TABLE 16

Triglyceride levels

| | Triglyceride levels ([Blood Triglyceride] mmol/L) |
|---|---|
| Control | 0.42 |
| THCV + CBD (both 0.3 mg/kg) | 0.55 |
| THCV + CBD (both 3.0 mg/kg) | 0.62 |

The triglyceride level was slightly increased with both the low and high dose THCV+CBD.

TABLE 17

Total cholesterol levels

| | Cholesterol levels ([Blood cholesterol] mmol/L) |
|---|---|
| Control | 5.5 |
| THCV + CBD (both 0.3 mg/kg) | 7.2 |
| THCV + CBD (both 3.0 mg/kg) | 4.1 |

As can be seen above the concentration of total cholesterol in the blood was vastly reduced by the higher dose combined THCV+CBD.

TABLE 18

HDL cholesterol levels

| | HDL cholesterol levels ([Blood HDL cholesterol] mmol/L) |
|---|---|
| Control | 2.00 |
| THCV + CBD (both 0.3 mg/kg) | 3.25 |
| THCV + CBD (both 3.0 mg/kg) | 3.00 |

The table above demonstrates how the HDL cholesterol concentration in the blood was dramatically increased by both the low and high doses of the combination of THCV+CBD.

Conclusions

Pure THCV+CBD BDS reduces percentage body fat;
Pure THCV+CBD BDS significantly increases energy expenditure (low & high dose);
Pure THCV+CBD BDS produced a major reduction in total cholesterol levels (high dose);
Pure THCV+CBD BDS produced a major increase in HDL cholesterol levels (low & high dose levels).

Example 3

The example described below investigated whether the cannabinoids, cannabidiol (CBD) and tetrahydrocannabivarin (THCV), act via the peroxisome proliferator-activated receptor gamma (PPARγ), which is known to be activated by $\Delta^9$-tetrahydrocannabinol.

Agonists of the PPARγ isoform improve insulin sensitivity and are often used in the management of type 2 diabetes. Additionally, PPARγ agonists have been shown to have positive cardiovascular effects, which include in vitro evidence of increased availability of nitric oxide (NO), and in vivo reductions in blood pressure and attenuation of atherosclerosis.

Some of the beneficial effects of PPARγ ligands are brought about by the anti-inflammatory actions of PPARγ activation, including inhibition of pro-inflammatory cytokines, increasing anti-inflammatory cytokines, and inhibition of inducible nitric oxide synthase (iNOS) expression. It is therefore thought that the use of PPARγ ligands might be a useful treatment option in the pharmaceutical management of metabolic syndrome or diseases and conditions associated with an increased risk of metabolic syndrome, and may therefore counter the side-effects associated with the use of atypical anti-psychotic medicaments.

In vitro vascular studies were carried out in rat isolated aortae by wire myography. PPARγ activation was investigated using reporter gene assays, a PPARγ competition-binding assay and an adipogenesis assay.

Both THCV and CBD were dissolved in ethanol to a stock concentration of 10 mM and further dilutions were made using distilled water.

Results:
Time-Dependent Effects of CBD and THCV in the Aorta

CBD (10 μM) caused significant time-dependent relaxation of the rat aorta compared to vehicle control at all time-points over the course of 2 h (2 h, vehicle 19.7±2.4% cf CBD 69.7±4.0% relaxation, n=13, P<0.001. After 2 h, the residual relaxation (the vasorelaxant effect of CBD minus the vasorelaxant effect of vehicle and time) was 50.1±3.3% relaxation.

CBD had no effect on basal tension over time (2 h, vehicle −0.02±0.01 g cf CBD −0.03±0.01 g, n=7).

In pre-contracted aortae, THCV (10 μM) had no effect on tone until after 105 minutes, and after 120 min, vasorelaxation to THCV was 28.7±4.6% relaxation (n=10), compared to 15.1±4.6% (P<0.01) in control arteries.

In the presence of the PPARγ receptor antagonist GW9662 (1 μM), the residual vasorelaxant effect of CBD was significantly reduced after 1 h of incubation. The vasorelaxant effect of CBD was similar in endothelium-denuded and control aortae. Similarly, in the presence of the nitric oxide synthase inhibitor, L-NAME (300 μM), the residual vasorelaxant effect of CBD was not different to that observed in control conditions.

The $CB_1$ receptor antagonist AM251 (1 μM) did not significantly affect the time-dependent vascular responses to CBD. The $CB_2$ receptor antagonist SR144528 (1 μM) significantly inhibited the residual vasorelaxant effects of CBD between 45 min to 90 min. Pre-treating arteries with either PTX (200 ng ml$^{-1}$, 2 h) or with capsaicin (10 μM, 1 h) had no effect on the vascular response to CBD over time.

When arteries were contracted with a high potassium buffer, there was no difference in the vasorelaxant effect of CBD compared with control. By contrast, in vessels where tone was induced with U46619 in calcium free buffer, the vasorelaxant effect of CBD was significantly blunted compared with control.

The potency and maximal contractile response to the re-introduction of calcium in calcium free, high potassium Krebs-Hensleit solution was significantly reduced in a concentration-dependent manner the presence of CBD from 1 μM to 30 μM. The calcium channel blocker, verapamil, caused significant vasorelaxation of pre-constricted vessels as CBD, although with a more rapid onset.

Effects of Chronic Treatment of Rats with CBD on Vascular Responses in Isolated Arteries Animals were treated for 2 weeks with either vehicle or CBD, and investigations of arterial function made.

In small resistance mesenteric vessels, the maximal contractile responses to methoxamine were significantly lower in CBD-treated animals than in vehicle-treated animals ($R_{max}$ 1.56±0.13 g vs CBD 2.20±0.13 g increase tension, n=7, P<0.001). CBD treatment caused an additional decrease in the potency of methoxamine ($pEC_{50}$ veh 5.94±0.08 vs CBD 5.79±0.10, P<0.05).

The maximal response to methoxamine in the aorta was also significantly higher in vehicle-treated animals (2.32±0.20 g increase tension, n=6) compared to CBD-treated animals (1.63±0.21 g increase tension, n=7, P<0.001).

Repeated treatment with CBD did not affect the vasorelaxant responses to acetylcholine in small resistance mesenteric arteries. However, in the aorta, CBD treatment significantly decreased the potency of acetylcholine ($pEC_{50}$ control 6.17±0.31 vs CBD-treated 5.37±0.40, n=6, P<0.01).

Transcriptional Transactivation Assays

To determine whether CBD stimulates PPARγ, transactivation assays were performed in homologous cells transiently overexpressing PPARγ and RXRα in combination with a luciferase reporter gene (3×PPRE TK luc).

In these assays, the synthetic PPARγ agonist rosiglitazone (10 μM) significantly stimulated the transcriptional activity of PPARγ compared to vehicle-treated cells transfected with all DNA (148±7 cf 319±7 relative luciferase activity (per ng ml$^{-1}$ protein), P<0.01).

Likewise, CBD also significantly stimulated the transcriptional activity of PPARγ compared to untreated-cells at 10 μM (305±18 relative luciferase activity, P<0.01) and 20 μM (470±37 relative luciferase activity, P<0.01) in a concentration-dependent manner.

THCV had no effect on PPARγ transcriptional activity at any concentration tested.

Induction of Adipocyte Differentiation

3T3L1 cells were cultured until confluent and then treated for 8 days with either CBD or rosiglitazone. Cells were fixed and stained with Oil Red O to identify fat droplets, to the presence of which indicates differentiation of fibroblasts into adipocytes. Untreated cells showed some signs of differentiation, but the majority of cells retained their spindle shape with little Oil Red O staining. Rosiglitazone induced differentiation of 3T3 L1 cells to adipocytes, as evidenced by large amounts of Oil Red O staining indicating fat droplet accumulation within the cytoplasm. In the presence of CBD, signs of fat droplet accumulation were apparent at all concentrations tested in a concentration-dependent manner.

Conclusions

These data provide strong evidence that CBD is a PPARγ agonist, and suggest a novel means by which the effects of CBD could be brought about. In light of the emerging evidence that PPARγ ligands have beneficial effects in type 2 diabetes, the cardiovascular system and potentially in a wide variety of other disorders including cancer, gastroinflammatory disorders and many skin diseases, these data provide evidence that cannabinoids could be useful in, amongst other things, the prevention of the metabolic symptoms associated with the use of anti-psychotic drugs.

Example 4

Methodology

Conditioned avoidance behavior was assessed using two automated shuttle-boxes (46 W×19.5 D×20 H cm, BIO MEDICA, Ltd) each placed in a sound-attenuated chamber. Each trial consisted of a 10 s warning tone (105 dB tone) as a conditioned stimulus (CS) followed by 10 s foot shock (1 mA) as an unconditioned stimulus (US) and 15-75 (mean; 45) s inter-trial interval. The US was terminated when the animal jumped over the hurdle from one compartment to the other or after a cut-off time of 10 s. Each rat was placed in one of the compartments of the shuttle box and allowed to freely explore it for 1 min before the first trial. During the training session, three kinds of responses were recorded:

- if crossing occurred in response to CS alone, a CAR was recorded;
- if crossing occurred during the period in which US was presented, an escape response was recorded;
- if the rats failed to react, an escape failure (EF) was recorded.

Animals
Species/Strain: rat/Wistar
Supplier: Japan SLC, Inc
Sex: male
Age (at time of beginning of training session): 6 weeks When the animal completed successfully an over 75% avoidance rate (15 CAR/20 trials) for 3 consecutive training sessions, it was defined as well-trained CAR and was used for evaluating the effects of compounds the next day.

Figure 2:
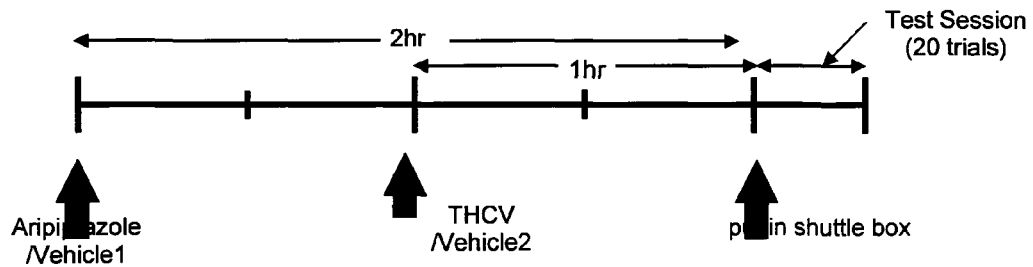
FIG. 2 illustrates the dosing regime in a conditioned avoidance experiment using the cannabinoid THCV with the atypical antipsychotic Aripiprazole.

The dosing regime for CBD is as illustrated in FIG. 1 and for THCV is illustrated in FIG. 2. (Vehicle 1: 5% Arabic gum, Vehicle 2: EtOH:chremohor:saline=1:1:18)

CBD and THCV were synthesized and used in this example.

Results

Example 4 i) Effect of Aripoprazole APZ (7.5 mg/kg po) and THCV (60 mg/kg ip) at Sub Effective Dose Levels (when Used Alone)

Figure 3:
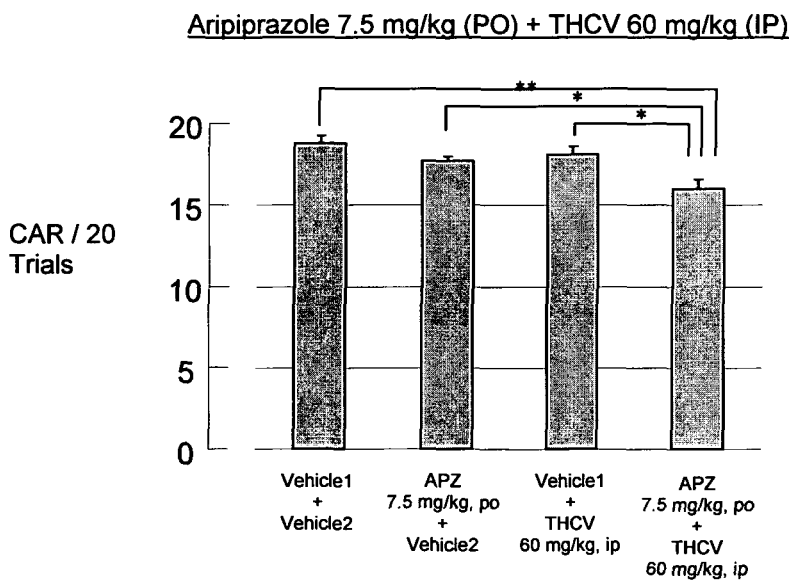
FIG. 3 illustrates the effects of THCV, APZ and the combination THCV and APZ at individually sub-effective doses.

The results are illustrated in FIG. 3 which is a bar chart showing the effect of:
Vehicle 1 and vehicle 2;
APZ and vehicle 2
THCV and vehicle 1; and
APZ and THCV.
Surprisingly a combination effect was detected.
*p<0.05, **p<0.01 (vs combination group) by 2-tailed Dunnett test, n=9-10
Vehicle 1: 5% Arabic gum
Vehicle 2: EtOH:chremohor:saline=1:1:18 ii) Effect of Aripoprazole APZ (15 mg/kg po) and THCV (60 mg/kg ip) at Effective Dose Levels (when APZ Used Alone)

Figure 4:
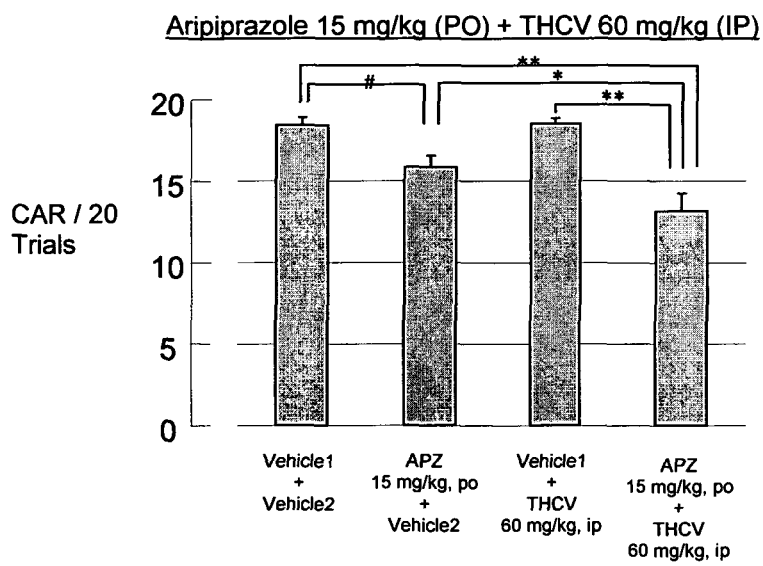
FIG. 4 illustrates the effects of THCV, APZ and the combination THCV and APZ at individually effective doses.

The results are illustrated in FIG. 4 which is a bar chart showing the effect of:
Vehicle 1 and vehicle 2;
APZ and vehicle 2
THCV and vehicle 1; and
APZ and THCV concentration.
Again a combination effect was observed at these doses on CAR.
*p<0.05, **p<0.01 (vs combination group) by 2-tailed Dunnett test, n=12
p<0.05 (vs Vehicle1+2 group) by 2-tailed Dunnett test
Vehicle 1: 5% Arabic gum,
Vehicle 2: EtOH:chremohor:saline=1:1:18

Example 5

Effect of CBD and THCV on Catalepsy (5a) and Ptosis (5b)

Figure 5:
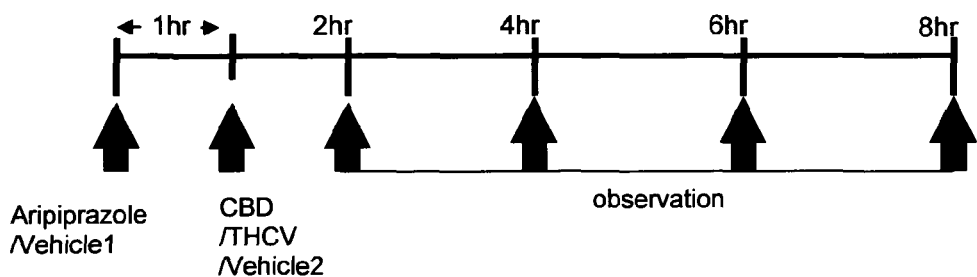
FIG. 5 illustrates the dosing regime used in a Catalepsy and Ptosis study with CBD and THCV respectively.

Methodology
Animals
Species/Strain: rat/Wistar
Supplier: Japan SLC, Inc
Sex: male
Age (at the test day): 6-7 weeks Animals were subjected to a protocol as illustrated in FIG. 5.
Vehicle 1: 5% Arabic gum,
Vehicle 2: EtOH:chremohor:saline=1:1:18

Rats were made to fast from 6 PM on the day before the experiment until sacrifice. Rats were weighed and orally (PO) administered aripiprazole. Then, rats were intraperitoneally (IP) injected cannabinoids (CBD and THCV) 1 hour after administration of aripiprazole. Catalepsy and ptosis were observed at 2, 4, 6 and 8 hours after the administration of aripiprazole. For measurement of catalepsy, the observations were performed three times at each observation time point. The animals were forced to hang with their right forepaw on the upper edge of a steel can (diameter: 6 cm, height: 10 cm). When the animals remained in the unnatural vertical position for 30 seconds or longer, they were judged to be positive responders for catalepsy.

The measurement of ptosis was performed as follows. Each animal was individually taken from the home cage and put on the experimenter's hand to observe the eyes. The ptosis score was determined for both eyes as described below, and the scores for the two eyes were added to obtain the total score (maximum score, 8)

0: Normal
1: Mild ptosis (upper eyelid covered ¼ of the eye)
2: Moderate ptosis (upper eyelid covered ½ of the eye)
3: Severe ptosis (upper eyelid covered ¾ of the eye)
4: Complete ptosis (upper eyelid covered the entire eye)

Results

Example 5a

Figure 6A:
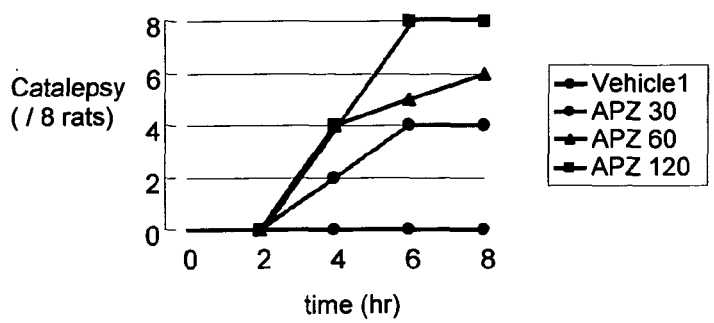
FIG. 6a illustrates the action of Aripiprazole alone.

The results at different doses are shown graphically in FIGS. 6a/6b (APZ/CBD) and FIGS. 6a/6c (APZ/THCV).

Figure 6B:
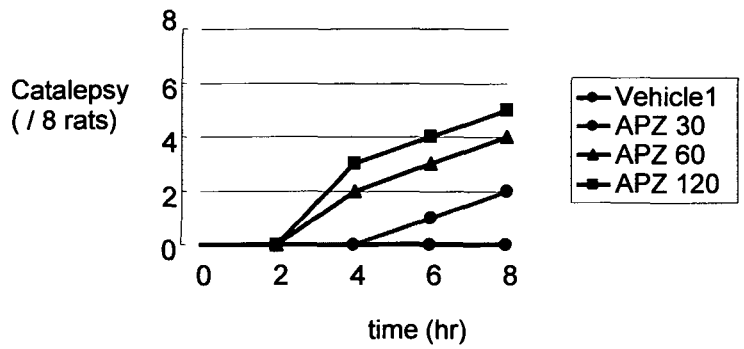
FIG. 6b illustrates the combination effect with CBD.

By comparison of FIG. 6a with FIG. 6b it is apparent that CBD (120 mg/kg, ip) significantly decreased Aripiprazole-induced catalepsy in rats (total, p=0.0286; 8 hr, p=0.0339, by generalized estimating equations). i.e. a combination effect was detected.
n=8,
Vehicle 1: 5% Arabic gum, Vehicle 2: EtOH:chremohor:saline=1:1:18

Figure 6C:
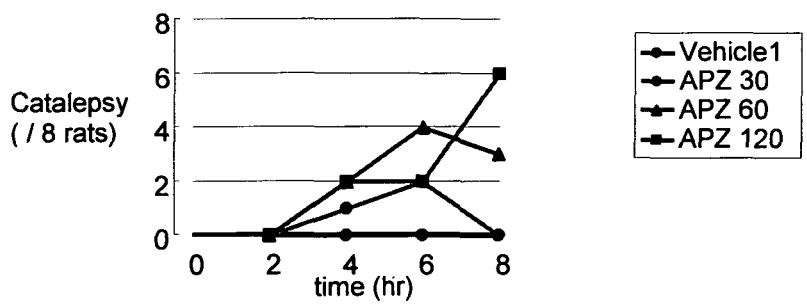
FIG. 6c illustrates the combination effect with THCV.

Similarly, by comparison of FIG. 6a with FIG. 6c it is apparent that THCV (60 mg/kg, ip) significantly decreased Aripiprazole-induced catalepsy in rats (total, p=0.0073; 8 hr, p=0.0060, by generalized estimating equations). i.e. a combination effect was detected.
n=8,
Vehicle 1: 5% Arabic gum, Vehicle 2: EtOH:chremohor:saline=1:1:18

CBD and THCV were synthesized and used in this example.

Example 5b

Figure 7:
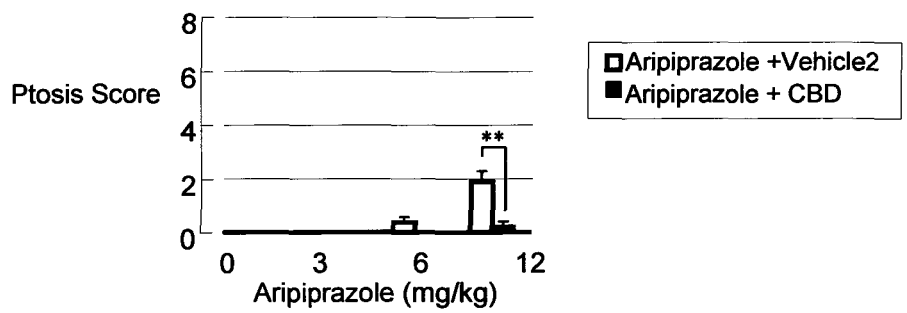
FIG. 7 illustrates the combination effect of Aripiprazole and CBD on Aripiprazole induced Ptosis.

The results are again shown graphically in FIGS. 7 (CBD) and 8 (THCV).

From FIG. 7 it is apparent that CBD (120 mg/kg, ip) significantly decreased Aripiprazole-induced ptosis in rats (Drug (CBD), p<0.01; Interaction, p<0.01, by 2-way ANOVA). i.e. a combination effect was detected.
**p<0.01 by Wilcoxon Rank Sum test with Bonferroni's correction, n=8,
Vehicle 1: 5% Arabic gum,
Vehicle 2: EtOH:chremohor:saline=1:1:18

Figure 8:
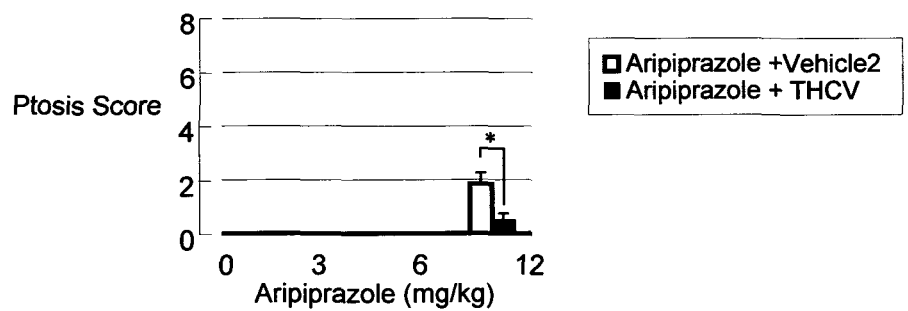
FIG. 8 illustrates the combination effect of Aripiprazole and THCV on Aripiprazole induced Ptosis.

Similarly from FIG. 8, it is apparent that THCV (60 mg/kg, ip) significantly decreased aripiprazole-induced ptosis in rats (Drug (THCV), p<0.01; Interaction, p<0.01, by 2-way ANOVA). i.e. a combination effect was detected.
*p<0.05 by Wilcoxon Rank Sum test with Bonferroni's correction, n=8,
Vehicle 1: 5% Arabic gum,
Vehicle 2: EtOH:chremohor:saline=1:1:18

CBD and THCV were synthesized and used in this example.

These examples, together with previously reported evidence, demonstrate how the use of a number of different phyto-cannabinoids in combination with anti-psychotic medicaments might be a more beneficial treatment than the use of the anti-psychotic medication alone as they may enable the reduction or removal of the undesirable side effects of the anti-psychotic drugs and may further provide additional anti-psychotic effects.

The invention claimed is:

1. A method for the treatment of psychosis or a psychotic disorder, which comprises administering to a subject in need thereof a therapeutically effective amount of THCV and/or CBD, in combination with a sub-effective dose of an atypical anti-psychotic medicament, wherein the THCV and/or CBD are administered separately, sequentially or simultaneously to the atypical anti-psychotic medicament so as to reduce or remove undesirable side effects of the atypical anti-psychotic medicament and/or provide additional anti-psychotic effects, wherein the atypical anti-psychotic medicament is a dopamine-serotonin system stabilizer.

2. A method for the treatment of psychosis or a psychotic disorder in a child or juvenile, which comprises administering to a subject in need thereof a therapeutically effective amount of THCV and/or CBD, in combination with a sub-effective dose of an atypical anti-psychotic medicament, wherein the THCV and/or CBD are administered separately, sequentially or simultaneously to the atypical anti-psychotic medicament so as to reduce or remove undesirable side effects of the atypical anti-psychotic medicament and/or provide additional anti-psychotic effects, wherein the atypical anti-psychotic medicament is a dopamine-serotonin system stabilizer.

3. The method as claimed in claim 1, wherein the undesirable side effects that are reduced or removed is obesity.

4. The method as claimed in claim 1, wherein the THCV and/or CBD are present in the form of a cannabis plant extract, which depending on the composition of the extract, has all or a proportion of THC or THCA selectively removed.

5. The method as claimed in claim 1, wherein the THCV and/or CBD are in the form of a botanical drug substance.

6. The method as claimed in claim 5, wherein the botanical drug substance comprises all the naturally occurring phyto-cannabinoids in the plant.

7. The method as claimed in claim 1, wherein the THCV and/or CBD in a substantially pure form.

8. The method as claimed in claim 1, wherein the THCV and/or CBD are in an isolated form.

9. The method as claimed in claim 1, wherein the THCV and/or CBD are in a synthetic form.

10. The method as claimed in claim 1, wherein the THCV and/or CBD are combined with the atypical anti-psychotic medicament and formulated as a pharmaceutical composition further comprising one or more pharmaceutically acceptable carriers, excipients or diluents.

11. The method as claimed in claim 1, wherein the atypical anti-psychotic medicament is selected from the group consisting of: aripiprazole; a metabolite of aripiprazole; risperidone; paliperidone; ziprasidone; olanzapine; quetiapine; clozapine; sulpiride; amisulpride; iloperidone; cariprazine; and asenapine.

12. The method as claimed in claim 11, wherein the atypical anti-psychotic medicament is aripiprazole or a metabolite of aripiprazole.

13. The method as claimed in claim 12, wherein the metabolite of aripiprazole is dehydroaripiprazole, OPC-14857, DM-1458, DM-1451, DM-1452, DM-1454 or DCPP.

14. The method as claimed in claim 1, wherein the psychosis or psychotic disorder to be treated is selected from the group consisting of: schizophrenia; schizophreniform disorder; schizoaffective disorder; bipolar I disorder; bipolar II disorder; major depressive disorder with psychotic feature; delusional disorders; Shared Psychotic Disorder; Brief Psychotic disorder; Psychotic disorder not otherwise specified; paranoid personality disorder; schizoid personality disorder; and schizotypal personality disorder.

15. The method as claimed in claim 14, wherein the schizophreniform disorder is acute schizophrenic episode.

16. The method as claimed in claim 14, wherein the bipolar I disorder is selected from the group consisting of: mania, manic disorder, and manic-depressive psychosis.

17. The method as claimed in claim 14, wherein the major depressive disorder with psychotic feature is psychotic depression.

18. The method as claimed in claim 14, wherein the delusional disorder is paranoia.

19. The method as claimed in claim 14, wherein Shared Psychotic Disorder is Shared paranoia disorder.

20. The method as claimed in claim 14, wherein the Brief Psychotic disorder is Unspecified Reactive Psychosis.

21. The method as claimed in claim 1, wherein the undesirable side effects that are reduced or removed are selected from the group consisting of: catalepsy; and ptosis.

* * * * *